United States Patent [19]

Murphy et al.

[11] Patent Number: 5,400,795
[45] Date of Patent: Mar. 28, 1995

[54] METHOD OF CLASSIFYING HEART RHYTHMS BY ANALYZING SEVERAL MORPHOLOGY DEFINING METRICS DERIVED FOR A PATIENT'S QRS COMPLEX

[75] Inventors: Anthony J. Murphy, Annandale; John Wickham, Fivedock; David Bassin, Coogee, all of Australia

[73] Assignee: Telectronics Pacing Systems, Inc., Englewood, Colo.

[21] Appl. No.: 141,805

[22] Filed: Oct. 22, 1993

[51] Int. Cl.⁶ .......................................... A61B 5/0472
[52] U.S. Cl. ................................................ 128/702
[58] Field of Search ................ 728/702, 703, 704, 705

[56] References Cited

U.S. PATENT DOCUMENTS

| | | | |
|---|---|---|---|
| 3,654,916 | 4/1972 | Neilson | 128/705 |
| 3,658,055 | 4/1972 | Abe et al. | 128/203 |
| 3,807,392 | 4/1974 | Harris | 128/702 |
| 4,453,551 | 6/1984 | Anderson et al. | 128/704 |
| 4,475,551 | 10/1984 | Langer et al. | 128/419 |
| 4,830,006 | 5/1989 | Haluska et al. | 128/419 |
| 5,000,189 | 3/1991 | Throne et al. | 128/702 |
| 5,058,599 | 10/1991 | Anderson | 128/705 |
| 5,086,772 | 2/1992 | Larnard et al. | 128/419 |

OTHER PUBLICATIONS

Automatic Tachycardia Recognition (Robert Arzbaecher, Thomas Bump, Janice Jenkins, Katherine Glick, Fran Munkenbeck, Jeffrey Brown, N. Nandhakumar) Pace, vol. 7 (II) pp. 541–547, May–Jun. 1984.

Tachycardia Detection In Implantable Antitachycardia Devices (Janice Jenkins, Thomas Bump, Fran Munkenbeck, Jeffrey Brown, Robert Arzbaecher) Pace, vol. 7 (II) pp. 1273–1277, Nov.–Dec. 1984.

Tachycardia Recognition By Implantable Electronic Devices (A. John Camm, D. Wyn Davies, David E. Ward) Pace, vol. 10 pp. 1175–1190, Sep.–Oct. 1987.

A Comparison Of Four New Time Domain Techniques For Discriminating Monomorphic Ventricular Tachycardia From Sinus Rhythm Using Ventricular Waveform Morphology (Robert D. Throne, Janice M. Jenkins, Lorenzo A. DiCarlo) IEEE Tr. on BioMed Eng. vol. 38(6), pp. 561–570, Jun. 1991.

Automatic Methods For Detection Of Tachyarrhythmias By Antitachycardia Devices (Frank Pannizzo, Anthony D. Mercando, John D. Fisher, Seymour Furman) Journal of American College of Cardiology, Vo. 11, pp. 308–316, Feb. 1988.

Engineering Aspects Of Implantable Defibrillators (Sanjeev Saksena, Nora Goldschlager) Electrical Therapy for Cardiac Arrhythmias: Pacing Antitachycardia Devices, Catheter Ablation published by W. B. Saunders, pp. 375–376 1990.

Introduction To Statistical Pattern Recognition (Keinosuke Fukuaga) Academic Press, Inc., London, Second Edition, pp. 124–169, 1990.

The Art Of Electronics (Paul Horowitz, Winfield Hill) The Art of Electronics (2nd Edition) Horowitz et al., Cambridge University Press, pp. 217–220, 1989.

Pattern Classification And Scene Analysis (Richard O. Duda, Peter E. Hart) John Wiley & Sons, pp. 24–31, 1973.

Primary Examiner—William E. Kamm
Attorney, Agent, or Firm—Gottlieb, Rackman & Reisman

[57] ABSTRACT

A method, useable in implantable cardioverter defibrillators, for classifying heart rhythms of a patient by means of electrogram morphology. A number of features (metrics) of the electrogram are measured to form a description of the shape of individual electrograms, and the metrics are then converted into a cardiac rhythm diagnosis by means of a pattern classification technique.

13 Claims, 2 Drawing Sheets

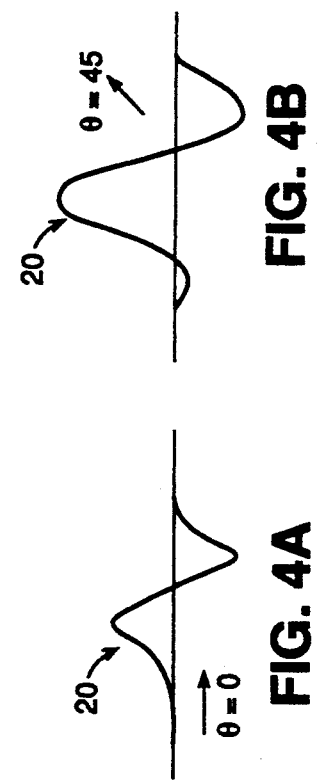
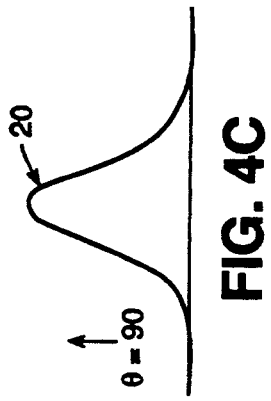
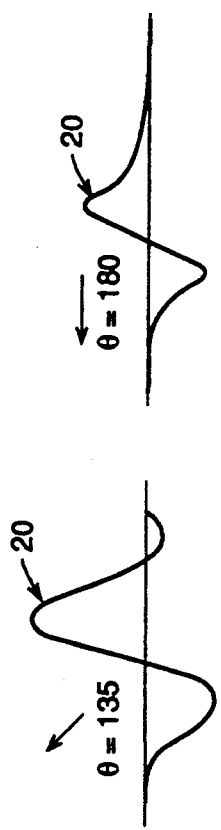
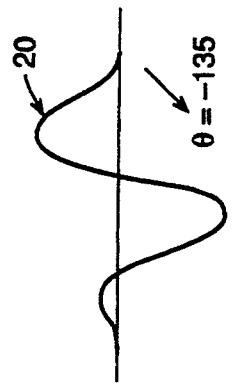
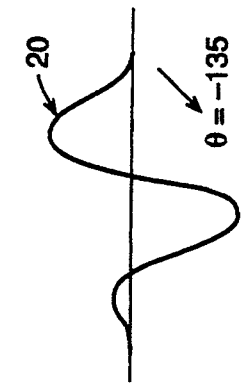
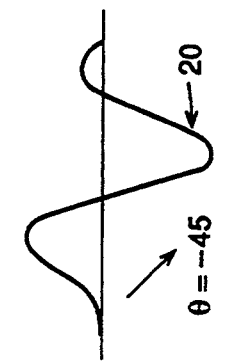
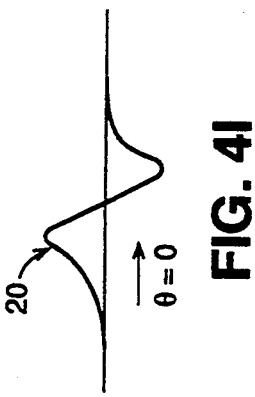
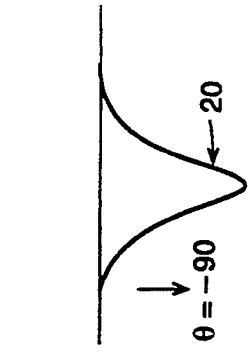

METHOD OF CLASSIFYING HEART RHYTHMS BY ANALYZING SEVERAL MORPHOLOGY DEFINING METRICS DERIVED FOR A PATIENT'S QRS COMPLEX

FIELD OF THE INVENTION

This invention relates to a method for classifying heart rhythms based on the shape (morphology) of the endocardial or epicardial electrogram. More particularly, a number of features (metrics) of the electrogram are measured to form a description of the shape of individual electrograms, and the metrics are then converted into a cardiac rhythm diagnosis by means of a pattern classification technique.

BACKGROUND OF THE INVENTION

There are a number of ways to discriminate different types of heart rhythm in an implantable cardioverter defibrillator (ICD). The most obvious way to do this is to use heart rate information alone, in the manner shown for example in U.S. Pat. No. 4,475,551 to Langer et al., entitled "Arrhythmia Detection and Defibrillation System and Method", which issued Oct. 9, 1984. The purpose of discriminating different rhythms in an ICD device is to allow the device to respond appropriately to each of them. Problems occur if there are two or more rhythms which require a different response from the device but cannot easily be discriminated from one another.

The rhythms which cause most problems in existing ICD devices are atrial fibrillation (AF) and sinus tachycardia (ST). Both of these rhythms can result in a ventricular rate that is high enough for it to be considered to be ventricular tachycardia (VT). Thus, VT cannot be discriminated from AF or ST on the basis of ventricular rate alone. Additional information must be used to correctly identify these rhythms.

As discussed in an article by Arzbaecher et al., entitled "Automatic Tachycardia Recognition", appearing in PACE, May-June 1984, Volume 7 (II), pages 541-547, and in an article by Jenkins et al., entitled "Tachycardia Detection in Implantable Antitachycardia Devices", appearing in PACE, Volume 7 (II), pages 1273-1277, November-December 1984, atrial fibrillation can be readily identified by looking at the ratio of the atrial rate to the ventricular rate. This requires the use of an atrial lead, however, which may be undesirable or unavailable. Also, this method is unsuited to discrimination of ST and VT, since both rhythms may exhibit a 1:1 ratio of atrial to ventricular rate.

Timing methods have been proposed for distinguishing ST or AF from VT (see, e.g., U.S. Pat. No. 4,830,006 to Haluska et al., entitled "Implantable Cardiac Stimulator for Detection and Treatment of Ventricular Arrhythmias", which issued on May 16, 1989, and see, e.g., an article by Camm et al., entitled "Tachycardia Recognition by Implantable Electronic Devices", appearing in PACE, September-October 1987, volume 10, pages 1175-1190). These methods are of dubious accuracy and some of them also require the use of an atrial lead.

The shape or morphology of the intracardiac electrogram can be used to achieve the desired discrimination between ST and VT.

Template methods of morphology analysis provide a scalar measure of the difference between two shapes. An example of normal morphology is established, and this is compared to each heartbeat for analysis. A scalar bound or threshold on the normal variation in this scalar measure is established, and any measure that exceeds this threshold is considered to represent an abnormal beat.

A number of template methods have been heretofore described (see, e.g., U.S. Pat. No. 5,000,189 to Throne et al., entitled "Method and System for Monitoring Electrocardiographic Signals and Detecting a Pathological Cardiac Arrhythmia Such as Ventricular Tachycardia", which issued on Mar. 19, 1991, and see, e.g., an article by Throne et al., entitled "A Comparison of Four New Time-Domain Techniques for Discriminating Monomorphic Ventricular Tachycardia from Sinus Rhythm Using Ventricular Waveform Morphology", appearing in IEEE Tr. on BioMed. Eng., Vol. 38 (6), at pages 561-570, (June 1991)). Template methods in general require high sampling rates and high processing overheads. For these reasons they are unsuited for use in an ICD.

Many attempts have been made to find a single metric that can be used for rhythm discrimination purposes (see, e.g., an article by Pannizzo et al., entitled "Automatic Methods for Detection of Tachyarrhythmias by Antitachycardia Devices", appearing in the Journal of American College of Cardiology at Vol. 11, pages 308-316, February 1988). A probability density function (PDF) algorithm has been of some utility in diagnosing ventricular fibrillation (VF), but has not proven successful for discriminating ST from VT. The PDF algorithm is discussed in the aforementioned U.S. Pat. No. 4,475,551 to Langer et al., and in an article by Bach et al., entitled "Engineering Aspects of Implantable Defibrillators," appearing in a book edited by Saksena et al., entitled "Electrical Therapy for Cardiac Arrhythmias: Pacing, Antitachycardia Devices, Catheter Ablation", published by W. B. Saunders, Philadelphia, 1990, at pages 375-376.

U.S. Pat. No. 5,086,772 to Larnard et al. describes a method for combining two simple morphological features with timing information to improve the rhythm discrimination process. This method considers first the rate, and uses the morphological information only in a specified rate band, to classify individual heartbeats. The cardiac rhythm is then diagnosed on the basis of the classification of a number of successive heartbeats. The present invention is a generalization of the Larnard et al. morphological method but its application is not limited thereby.

It is, therefore, a primary object of this invention to provide an improved method of classifying heart rhythms by means of electrogram morphology.

It is another object of this invention to provide an improved method of classifying heart rhythms by means of electrogram morphology, which method is usable in an implantable cardioverter defibrillator.

It is a still further object of this invention to provide a method of classifying heart rhythms by means of electrogram morphology, which method employs a low sampling rate, requires very few multiplications per heartbeat classification, consumes very little power in the classification process, and can be implemented both in digital and analog electronics.

Further objects, features and advantages of the invention will become apparent as the following description proceeds.

SUMMARY OF THE INVENTION

Briefly stated, and in accordance with one embodiment of this invention, a number of metrics are used simultaneously to improve the accuracy of the classification decision process. Bounds on the normal variation of the metrics are established. These bounds define a decision surface which divides the measurement space into two regions. Measurement vectors which fall in one of these regions are considered to represent normal heartbeats, while those that fall in the other region are considered to represent abnormal heartbeats. Methods for achieving this have been discussed by K. Fukunaga in a book entitled "Introduction to Statistical Pattern Recognition", published by Academic Press, Inc., London, Second Edition, pp. 124–169, 1990, and by Duda et al., in a book entitled "Pattern Classification and Scene Analysis", published by John Wiley & Sons, New York, pp. 24–31, 1973. The particular metrics disclosed in the present invention require only simple operations and low sample rates to calculate. Further, the method for reaching a rhythm classification based on these metrics imposes a very small computational burden. Thus, this method is ideally suited for use in ICDs.

The shape of the electrogram is quantified by measuring particular features thereof, such as amplitude or width. The value of these features are the metrics, and a set of metrics form a quantitative description of the shape of an electrogram. The shape of an electrogram is then indirectly compared to that of a known normal electrogram by comparing the metrics, and a given heartbeat is then classified as either normal or abnormal. VT may then be diagnosed if a number of successive heartbeats are abnormal.

The metrics that are discussed here are simple ones that can be implemented either in analog electronics, or with low computational overhead on a microprocessor. They require only such techniques as filtering, peak-picking, thresholding, and integrating. Further, by use of a peak-holding sampling process, they can be calculated from a very low data rate digital signal. The rate of 80 Hz has been shown to be sufficient. A suitable set of metrics that may be employed in connection with diagnosing a rhythm are the area under the electrogram (hereinafter defined more completely and referred to as "MOD"), the peak-to-peak amplitude (hereinafter defined more completely and referred to as "PKP"), and the amplitude of the largest negative peak (hereinafter defined more completely and referred to as "NVE").

The electrogram signal is filtered, preferably with a passband of two to thirty Hz ($-3dB$). The lowpass section of the filter serves as an antialiasing filter, and smooths the transitions in the electrogram so that peaks may easily be identified. The highpass section of the filter serves to remove any baseline wander from the signal, so that a separate DC removal stage is not required.

The filtered signal is sampled at a rate that can be as low as 80 Hz, using a known peak-holding method, such as the one discussed at pages 217–220 in the book "The art of Electronics" (2nd Ed.), authored by P. Horowitz and W. Hill, published by Cambridge University Press, Cambridge, U.K. (1989). Alternatively, the metrics may be measured directly using analog electronics. The values of the metrics are calculated for a known segment of normal sinus rhythm (NSR). The mean of the NSR value (hereinafter "NSR-mean") for each metric is stored for later use.

When a rhythm is to be diagnosed, the NSR-mean is subtracted from each measured metric in the unknown rhythm. This gives the NSR-mean-removed metrics. If the unknown rhythm is in fact ST, then the values of all the NSR-mean removed metrics will be small, because the shape of the electrogram will be similar to that in NSR. If the rhythm is VT, however, then at least one (and usually more) of the NSR-mean-removed metrics will be large. This difference is detected by the classification process, which is described below.

The classification process includes a classifier, hereinafter described in greater detail and referred to as the "SUM classifier". The SUM classifier is an improvement over previously known methods of classification theory. It provides similar performance at a much reduced computational load compared to previously known methods. In a step-wise fashion, the SUM classifier performs the following operations:

a) Filters the electrogram;
b) Calculates the raw metrics from the filtered electrogram;
c) Amplitude-normalizes the metrics;
d) Subtracts off the NSR-means;
e) Subtracts off the ST-offsets;
f) Takes the absolute values (to get error terms);
g) Weights the error terms with weighting parameters;
h) Sums the weighted error terms (to get the error sum); and
i) Compares the error sum to a threshold. The foregoing steps give a classification of successive heartbeats as either normal or abnormal. A normal rhythm (i.e., sinus tachycardia) is then defined as a rhythm that contains some number of normal heartbeats in a specified number of heartbeats, for example 7 or more normal heartbeats in the last 10 heartbeats.

The metrics values are largely insensitive to filter corner frequencies. Sample rate also has little effect on performance, provided that peak-holding is employed. Good performance has been demonstrated at sample rates as low as 80 Hz, as indicated earlier.

Quantization of the signal to 8 bits causes only a small degradation in performance, and this is the recommended signal resolution. It may be possible to quantize the signal further, but this has not been tested.

The advantages of the method of the present invention for use in ICD's are, thus, that it employs a low sampling rate, requires very few multiplications per heartbeat, consumes low power, and can be implemented in analog electronics.

DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

FIGS. 4A–4I show the values of the QRS metric for a number of representative wave shapes.

DESCRIPTION OF THE PREFERRED EMBODIMENT

Figure 1:
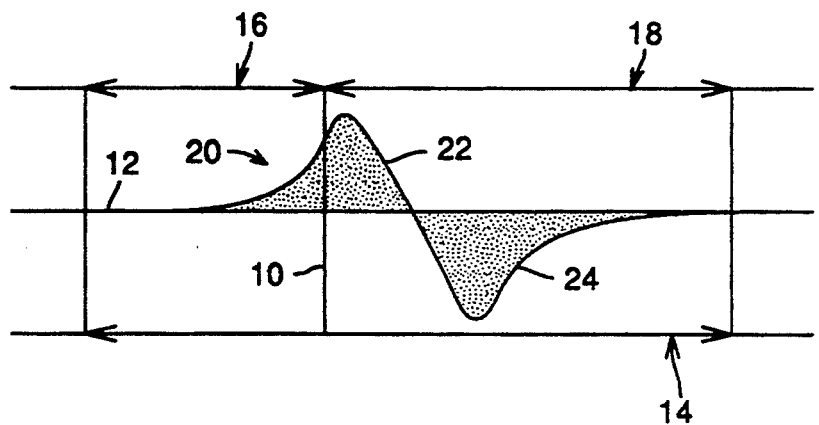
FIG. 1 shows the method of calculation of the MOD metric.

A number of concepts recur in the following description of the metrics. Referring to FIG. 1, which illustrates a QRX complex 20 of an electrogram, the fiducial point or sensing point is shown at 10. The fiducial point 10 is a timing reference within the electrogram. In the simplest case the fiducial point is the point at which a sensing circuit (not shown) is tripped. The fiducial point that is currently used is the time of greatest dV/dt (slew) of the electrogram or, equivalently, the time at which the high-pass-filtered electrogram has the greatest excursion from a baseline 12.

An analysis window 14 is defined in terms of absolute offsets 16 and 18 from the fiducial point 10. In tests that have been performed utilizing the present method, the analysis window 14 has been set at 100 ms wide, centered on the fiducial point 10. The width of the analysis window 14 is not critical, but should extend out to the isoelectric segments on either side of the QRS complex 20 under consideration. Incoming (raw) data is filtered in an analysis filter (not shown) before any metric analysis is performed on the incoming data stream. The analysis filter removes low frequency base line wander, and high frequency noise. It also serves as an antialiasing filter. The analysis filter is preferably a first order 2 Hz highpass filter, followed by a second order 30 Hz Butterworth low pass filter.

In the discussions which follow, references to an electrogram are intended to mean the electrogram at the output of the analysis filter, with the exception of the metric hereinafter referred to as "FIL" metric, which metric uses a bandpass filter (not shown, but hereinafter discussed) in place of the 30 Hz Butterworth low pass filter.

The following metrics which may be used in connection with the present invention will now be described in greater detail: MOD, PK, PVE, NVE, PKP, DIF, FIL, SSA, QRS and ORD.

MOD Metric

The MOD metric is the absolute (modulus) area under the QRS complex 20 of FIG. 1. It is shown shaded at 22 and 24 in that figure. The MOD metric is defined as the SUM of absolute values of the samples within the analysis window 14. For an analogue implementation, the MOD metric would be defined in terms of an integral. This metric is intended to reflect the width of the complex 20 of the electrogram.

PK Metric

The PK metric is the value of the largest excursion of the electrogram complex 20 from the base line 12. It is signed so that if the largest peak is negative, than the PK metric is negative, and if the largest peak is positive (see, e.g. deflection 28 in FIG. 3), then the PK metric is positive. It reflects both the amplitude and polarity of the electrogram complex 20.

PVE and NVE metrics

The PVE metric is the amplitude of the largest positive deflection (see, e.g. deflection 28 in FIG. 3) in the electrogram complex 20. Similarly, the NVE metric is the amplitude of the largest negative deflection (see, e.g., deflection 30 in FIG. 3) in the electrogram complex 20.

PKP metric

Figure 2:
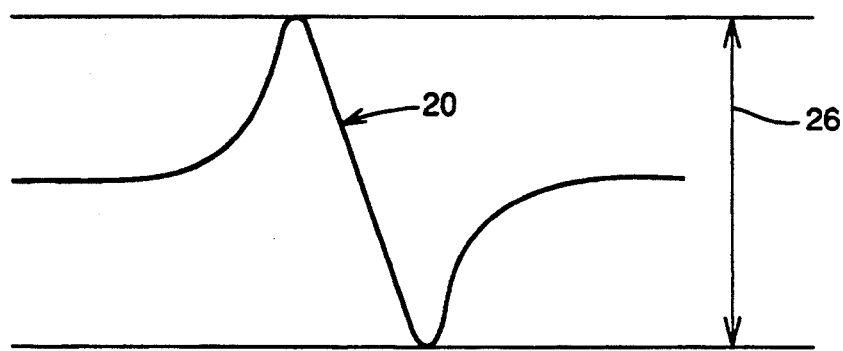
FIG. 2 shows the method of calculation of the PKP metric.

The PKP metric is the peak-to-peak amplitude of the electrogram complex, and is shown in FIG. 2 at 26. This is the absolute amplitude of the largest positive deflection plus the absolute amplitude of the largest negative deflection. It reflects the amplitude of the electrogram complex 20.

DIF metric

Figure 3:
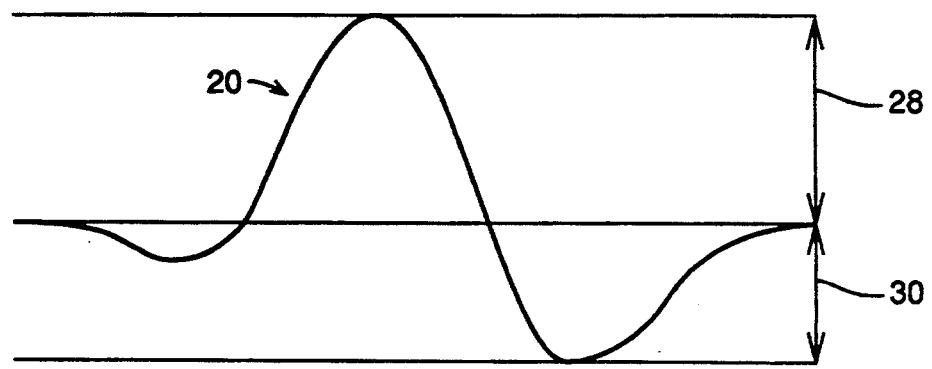
FIG. 3 shows the method of calculation of the DIF metric.

Referring to FIG. 3, the DIF metric is the difference between the absolute amplitudes of the largest positive deflection 28 of the electrogram complex 20 and the largest negative deflection 30 of the electrogram complex 20. The DIF metric will be large and positive for an upright electrogram complex, small for a biphasic one, and large and negative for an inverted one. Thus, the DIF metric is a continuous variable which reflects the polarity of the QRS complex of the electrogram.

FIL metric

The FIL metric is the peak-to-peak amplitude of a filtered version of the electrogram. The raw signal is passed through a filter having the following characteristics: single pole high pass at 2 Hz, two pole band pass, and Q=1 at 25 Hz. The peak-to-peak amplitude of this signal is measured in the same way that the PKP metric is measured. This metric is designed to reflect the slew rate (dV/dt) of the electrogram complex 20. The high pass characteristic in the filter acts as a differentiator.

SSA metric

The SSA metric is the signed-square area metric. It is an integral measure, like the MOD metric. It is calculated as follows: for each sample within the analysis window the sample is squared and its sign is restored (e.g., $2^2=4$; $-2^2=-4$). Then the signed squares are summed, the square root of the absolute value of the sum is taken, and the sign is restored. This gives a measure having characteristics similar to those of the DIF metric, i.e., it forms a continuous variable that reflects the polarity of the electrogram. The squaring is used to ensure that a large amplitude narrow lobe in the electrogram will predominate over a smaller amplitude but wider one. This is necessary because the high pass characteristic in the analysis filter will often produce a wide, low amplitude lobe in the filtered electrogram. The following is a mathematical description of the SSA metric:

$$t = \Sigma(\text{sign}(x) \cdot x^2)$$

$$SSA = \text{sign}(t) \cdot \sqrt{|t|}$$

ORS metric

Referring to FIGS. 4A–4I, the QRS metric represents the QRS angle Θ as calculated from the amplitude and temporal order of the largest positive and largest negative peaks, as follows:

r = abs(smaller peak ÷ larger peak)

Φ = arcos(r)

If the first peak is positive and larger: Θ=Φ
If the first peak is positive and smaller: Θ=−Φ
If the first peak is negative and larger: Θ=Φ−180
If the first peak is negative and smaller: Θ=180−Φ

ORD metric

The ORD metric reflects the order of the peaks in the electrogram complex 20. It is used in conjunction with the DIF metric to replace the QRS metric. The ORD metric is defined as follows:

If the positive peak is first, ORD=smaller peak÷larger peak.

If the negative peak is first ORD=—smaller peak ÷larger peak.

This gives a metric (ORD) which is a continuous variable that reflects order. Thus, if the electrogram complex 20 is biphasic with the positive peak first, the result is close to one; if it is biphasic with the negative peak first, the result is close to minus one; if it is monophasic, the result is close to zero.

The ORD and DIF metrics, in combination, would give ordered pairs of numbers that correspond very roughly to the QRS angles Θ of FIGS. 4A–4I, as shown in Table 1 below:

TABLE 1

| Relationship Among QRS, ORD and DIF Metrics | |
|---|---|
| QRS angle Θ | (DIF,ORD) |
| 0 | (0.0,1.0) |
| 45 | (0.5,0.5) |
| 90 | (1.0,0.0) |
| 135 | (0.5,−0.5) |
| 180 (= −180) | (0.0,−1.0) |
| −135 | (0.5,−0.5) |
| −90 | (−1.0,0.0) |
| −45 | (−0.5,0.5) |

All three of the metrics QRS, ORD and DIF suffer from the problem that they represent a two-point description of the electrogram complex 20, and some electrogram complexes necessarily require three points to properly describe them. They are simple to implement, however, requiring only positive and negative peak pickers (not shown), which are needed in any event for other metrics.

As will be discussed in greater detail hereinafter, tests were performed to determine the correlation between various parameters. All of the metrics, except QRS angle Θ, were highly correlated with each other. This is because they all depend very strongly on the amplitude of the electrogram complex 20. This does not represent a problem for the PK and PKP metrics, which are intended to reflect the amplitude of the electrogram. However, it is unsatisfactory for the other metrics, which end up reflecting the amplitude more strongly than the desired feature. The result is a large collection of amplitude measures, and very little else.

Amplitude Normalization

To resolve the foregoing problem, metrics that have an unwanted sensitivity to amplitude are normalized in accordance with this invention. Such normalization is achieved by dividing the metrics in question by the PKP metric. This results in a set of metrics which are only loosely correlated with each other. Thus, they should reflect different aspects of the shape of the electrogram complex, as is desired. It is preferable to always use the MOD, PVE, NVE, DIF, FIL and SSA metrics in the normalized form.

This process of amplitude normalization is preferably integrated into the SUM classifier, described below, enabling the number of computer operations to be minimized.

SUM classifier

The SUM classifier for the metrics involves a complex process which decides if a particular measurement resides in a region of the measurement space that is considered normal (to be classed as ST). If the measurement falls outside of this region, it will classed as VT. Using the metrics MOD, PKP, and NVE, the measurement space will be three dimensional, and the normal region will be a three dimensional space around the mean of the ST measurements.

The goal of the SUM classifier is to minimize the computational cost of its operation. This is primarily dependent on the number of multiplications made per heartbeat.

Given a three dimensional feature vector, for example the three measurements MOD, PKP and NVE, denoted m, p and n, respectively, and a set of weights ($\alpha$, $\beta$, and $\gamma$) the SUM classifier is defined as:

$$\alpha|m - \bar{m}_{ST}| + \beta|p - \bar{p}_{ST}| + \gamma|n - \bar{n}_{ST}| \begin{matrix} ST \\ < \\ > \\ VT \end{matrix} T \quad (1)$$

The above expression means that if the weighted sum of the distance of the measurement from the ST mean (ST offsets) is less than some threshold (T), the measurement will be classified as ST; otherwise, it would be classified as VT. Stated another way, it means that if the measurement is similar to the ST mean it will be classified as ST, and if it is dissimilar, it will be classified as VT.

The foregoing discussion assumes that the measured metrics would be used directly. In fact, they must be processed somewhat before being used in the SUM classifier. Firstly, the m (MOD) and n (NVE) metrics need to be normalized by division by the p (PKP) metric, as follows:

$$m' = \frac{m}{p} \quad (2)$$

$$n' = \frac{n}{p} \quad (3)$$

The NSR-mean is then subtracted from the normalized metrics:

$$m'' = m' - \hat{m}'_{NSR} = \frac{m}{p} - \hat{m}'_{NSR} \quad (4)$$

$$p'' = p - \hat{p}_{NSR} \quad (5)$$

$$n'' = n' - \hat{n}'_{NSR} = \frac{n}{p} - \hat{n}'_{NSR} \quad (6)$$

where $\hat{m}'_{NSR}$, for example, is the mean of the normalized value of the MOD metric, calculated in NSR.

The discriminant function is thus:

$$\alpha\left|\frac{m}{p} - \hat{m}'_{NSR} - \bar{m}''_{ST}\right| + \beta|p - \hat{p}_{NSR} - \bar{p}''_{ST}| + \gamma\left|\frac{n}{p} - \hat{n}'_{NSR} - \bar{n}''_{ST}\right| \begin{matrix} ST \\ < \\ > \\ VT \end{matrix} T \quad (7)$$

This must be reorganized firstly to remove divisions, and then to minimize the number of multiplies that must be performed beat-by-beat:

$$\frac{\alpha}{T}|m - p(\hat{m}'_{NSR} + \bar{m}''_{ST})| + p\frac{\beta}{T}|p - (\hat{p}'_{NSR} + \bar{p}''_{ST})| + \quad (8)$$

-continued $$\frac{\gamma}{T} |n - p(\hat{n}'_{NSR} + \bar{n}''_{ST})| \underset{VT}{\overset{ST}{\lessgtr}} p \quad (5)$$

where $$\frac{\alpha}{T}, \frac{\beta}{T}, \frac{\gamma}{T},$$

$\bar{m}''_{ST}$, $\bar{p}''_{ST}$ and $\bar{n}''_{ST}$ are parameters (and so need not be calculated beat-by-beat), and $$\hat{m}'_{NSR} = \frac{1}{N} \sum_{i=0}^{N-1} \frac{m_i}{p_i} \quad (9)$$

$$\hat{p}'_{NSR} = \frac{1}{N} \sum_{i=0}^{N-1} p_i \quad (10)$$

$$\hat{n}'_{NSR} = \frac{1}{N} \sum_{i=0}^{N-1} \frac{n_i}{p_i} \quad (11)$$

are calculated by background processes during NSR. This updating preferably occurs at a programmable interval in the range of 10 minutes to 1 hour. Thus, the number of multiplications required per complex during a rhythm classification is six.

The terms $\alpha$, $\beta$ and $\gamma$ are calculated as the differences between the inverse of the square root of the diagonal terms of the class covariance matrices K, described in greater detail below.

The classifier parameters for use in an implant are calculated from a set of metrics produced by the real implant hardware and software. The parameters $\alpha$, $\beta$, $\gamma$, $\bar{m}''_{ST}$, $\bar{p}''_{ST}$, and $\bar{n}''_{ST}$ are preferably programmable, but should not be available to the physician. This will allow the performance of the system to be tuned. The threshold parameter T (or an offset on the threshold) could be made available to the physician. This would allow a trade-off between sensitivity and specificity.

In order to more clearly understand the term "covariance matrices K", referred to above, the following tutorial material with respect to random variables is provided.

The expectation or mean of a random vector "x" is a vector "m" defined as:

$$m = E[x] = \int_{-\infty}^{\infty} x p_x(x) dx \quad (12)$$

where $p_x(x)$ is the probability density at x. This is taught by Therrien, C. W., in the book "Decision Estimation and Classification", published by John Wiley and Sons, New York, 1989, (hereinafter referred to as "Therrien"), at equation 2.41, page 24.

When training a classifier from a limited data set, this is estimated as:

$$\hat{m}_i = \frac{1}{N_i} \sum_{j=0}^{N_i-1} x_{ij} \quad (13)$$

where $x_{ij}$ is the j'th observation vector for class i; $N_i$ is the number of observations of class i; and $\hat{m}_i$ is the estimate of the mean vector of class i.

The covariance matrix "K" of a random vector "x" with expectation "m" is defined as:

$$K = E[(x - m)(x - m)^T] \quad (14)$$

where T is a matrix transposition operator (Therrien, page 49); and E is an expectation operator (Therrien, equation 12, page 54). (Also, see Therrien, equation 4.42, page 55).

When training a classifier from a limited data set, this is estimated as:

$$\hat{K}_i = \frac{1}{N_i} \sum_{j=0}^{N_i-1} (x_{ij} - \hat{m}_i)(x_{ij} - \hat{m}_i)^T \quad (15)$$

where $\hat{K}_i$ is the estimate of the covariance matrix of class i.

The SUM classifier relies on a specific discriminant function. Accordingly, the following discussion, relating to decision rules and discriminant functions, is presented at this time.

The decision rule for for the two-class case takes the form:

$$f(\hat{y}) \underset{\omega_2}{\overset{\omega_1}{\lessgtr}} T \quad (16)$$

The interpretation of this expression is as follows. If some function f() of the observation vector $\hat{y}$ is less than some threshold T, then assign the class label $\omega_1$ to it; otherwise assign the class label $\omega_2$.

The SUM classifier is derived from a Gaussian quadratic classifier, which is well known in the literature. Accordingly, the following discussion relating to the Gaussian quadratic classifier is provided.

The Gaussian quadratic classifier provides a Bayes optimal solution if the class conditional probability density functions are Gaussian. If the density functions are not Gaussian, then the probability of error is not minimised. The resulting classifier provides a decision surface which is best matched to the second moment statistics. (See, Therrien, pages 96,97).

A general two-class quadratic classifier is defined as follows:

$$h(y) = \hat{y}^T A \hat{y} + b^T \hat{y} + c \underset{\omega_2}{\overset{\omega_1}{\lessgtr}} T \quad (17)$$

(See Therrien, equation 6.6, page 96).

This resulting classifier will be Gaussian quadratic if the classifier parameters are defined as follows:

$$A = K_1^{-1} - K_2^{-1} \quad (18)$$

$$b = 2(K_2^{-1} m_2 - K_1^{-1} m_1) \quad (19)$$

$$c = m_1^T K_1^{-1} m_1 - m_2^T K_2^{-1} m_2 + \ln \left| \frac{K_1}{K_2} \right| \quad (20)$$

The derivation of the SUM classifier, starting with the equation for the discriminant function of the Gaussian quadratic classifier, is set forth below. It develops the equations to calculate the parameters of the sum classifier, viz. alpha, beta, and gamma.

The discriminant function for the SUM classifier can be derived from the Gaussian quadratic discriminant function, which can be written as:

$$h(y) = (y - m_1)^T K_1^{-1}(y - m_1) - \qquad (21)$$

$$(y - m_2)^T K_2^{-1}(y - m_2) + \ln\left|\frac{K_1}{K_2}\right|$$

In practice this will be compared to a threshold (for a two-class problem):

$$h(y) \begin{array}{c} \omega_1 \\ < \\ > \\ \omega_2 \end{array} T \qquad (22)$$

Thus the log of the covariance determinants can be considered as part of the threshold value T, resulting in the simpler form:

$$h'(y) = (y-m_1)^T K_1^{-1}(y-m_1) - (y-m_2)^T K_2^{-1}(y-m_2) \qquad (23)$$

If we set the class 2 (VT) mean to be equal to the class 1 (ST) mean, we can make the substitution:

$$y' = y - m_1 \qquad (24)$$

The discriminant function thus becomes:

$$h''(y') = y'^T(K_1^{-1} - K_2^{-1})y' \qquad (25)$$

If we set the off-diagonal terms for the covariance matrices to be zero, this becomes (for three features):

$$h'''(y') = \qquad (26)$$

$$y'^T \left\{ \begin{vmatrix} \frac{1}{\sigma_{a1}^2} & 0 & 0 \\ 0 & \frac{1}{\sigma_{b1}^2} & 0 \\ 0 & 0 & \frac{1}{\sigma_{c1}^2} \end{vmatrix} - \begin{vmatrix} \frac{1}{\sigma_{a2}^2} & 0 & 0 \\ 0 & \frac{1}{\sigma_{b2}^2} & 0 \\ 0 & 0 & \frac{1}{\sigma_{c2}^2} \end{vmatrix} \right\} y'$$

which reduces to:

$$h'''(y') = \qquad (27)$$

$$y'^T \left\{ \begin{vmatrix} \frac{1}{\sigma_{a1}^2} - \frac{1}{\sigma_{a2}^2} & 0 & 0 \\ 0 & \frac{1}{\sigma_{b1}^2} - \frac{1}{\sigma_{b2}^2} & 0 \\ 0 & 0 & \frac{1}{\sigma_{c1}^2} - \frac{1}{\sigma_{c2}^2} \end{vmatrix} \right\} y'$$

which reduces to:

$$h'''(y') = y_a'^2\left[\frac{1}{\sigma_{a1}^2} - \frac{1}{\sigma_{a2}^2}\right] + y_b'^2\left[\frac{1}{\sigma_{b1}^2} - \frac{1}{\sigma_{b2}^2}\right] + \qquad (28)$$

$$y_c'^2\left[\frac{1}{\sigma_{c1}^2} - \frac{1}{\sigma_{c2}^2}\right]$$

From the above we see that the discriminant function is a weighted sum-of-square distance measure. (It actually measures the distances from the ST class mean, which intuitively makes sense.)

In the special case where: $\sigma_{a1}^2 < \sigma_{a2}^2$, $\sigma_{b1}^2 < \sigma_{b2}^2$, and $\sigma_{c1}^2 < \sigma_{c2}^2$ this can be re-cast using a sum-of-absolute-values distance measure, giving:

$$h(y') = \alpha|y_a'| + \beta|y_b'| + \gamma|y_c'| \qquad (29)$$

where the coefficients $\alpha$, $\beta$, and $\gamma$ of the SUM classifier are thus calculated from the diagonal terms of the class covariance matrices as follows:

$$\alpha = \sqrt{\frac{1}{\sigma_{a1}^2} - \frac{1}{\sigma_{a2}^2}} \qquad (30)$$

$$\beta = \sqrt{\frac{1}{\sigma_{b1}^2} - \frac{1}{\sigma_{b2}^2}} \qquad (31)$$

$$\gamma = \sqrt{\frac{1}{\sigma_{c1}^2} - \frac{1}{\sigma_{c2}^2}} \qquad (32)$$

In practice it has been found sufficient to approximate this as follows:

$$\alpha = \frac{1}{\sigma_{a1}} - \frac{1}{\sigma_{a2}} \qquad (33)$$

$$\beta = \frac{1}{\sigma_{b1}} - \frac{1}{\sigma_{b2}} \qquad (34)$$

$$\gamma = \frac{1}{\sigma_{c1}} - \frac{1}{\sigma_{c2}} \qquad (35)$$

It will be apparent from the foregoing description that the present invention provides a method of classifying heart rhythms by means of electrogram morphology, which method may be used in implantable cardioverter defibrillators, involves a low sample rate, very few multiplications per heart beat, can be implemented in digital as well as analog electronics, and consumes very little power.

While particular embodiments of this invention have been shown and described, it will be obvious to those skilled in the art that various other changes and modifications may be made without departing from this invention in its broader aspects. For example, the MOD, PKP and NVE metrics are not the only suitable set of metrics that may be employed with this invention. Many other combinations of the metrics described herein may also be used. Similarly, other metrics may be devised that might also work well. In addition, the parameters of the SUM classifier could be calculated using equations 30–32, rather than 33–35. Alternatively, any other type of classifier known to the art could be substituted for the SUM classifier. These include discriminant function, K-nearest neighbors, neural network, etc. It is, therefore, aimed in the appended claims to cover all such changes and modifications as fall within the true spirit and scope of this invention.

What is claimed is:

1. A method of classifying heart rhythms of a patient by means of electrogram morphology, comprising the steps of:

storing a first set of at least two morphology-defining metrics derived from a QRS complex of a normal electrogram, said electrogram having a width and an amplitude, said metrics defining the shape of said electrogram including at least one of said width and amplitude;

establishing bounds of normal variation for said metrics which are combined to define a decision surface that includes first and second regions such that said first region represents normal heartbeats and said second region represents abnormal heartbeats;

providing an electrogram of a patient's heart rhythm;

measuring a second set of metrics for a given heartbeat from said patient's electrogram, said metrics of said second set corresponding to said metrics of said first set;

comparing the metrics of said second set with the metrics of said first set to decide which of said regions said given heartbeat falls into and to classify said given heartbeat as either normal or abnormal based on said decision;

repeating said measuring and comparing steps for a plurality of times; and, if a number of heartbeats are found to be abnormal, diagnosing the patient's heart rhythm as ventricular arrhythmia.

2. A method according to claim 1, wherein said storing step includes a sub-step of storing a first set of at least three metrics selected from a group of metrics that includes: a MOD metric, which comprises an absolute area under a QRS complex of a normal electrogram; a PK metric, which comprises a value of a largest excursion of said QRS complex from its baseline, said value having the same polarity as said excursion; a PVE metric, which comprises an amplitude of a largest positive deflection of said QRS complex; a NVE metric, which comprises an amplitude of a largest negative deflection of said QRS complex; a PKP metric, which comprises a peak-to-peak amplitude of said QRS complex; a DIF metric, which comprises the difference between the absolute amplitudes of the largest positive deflection of said QRS complex and the largest negative deflection of said QRS complex; a FIL metric, which comprises a peak-to-peak amplitude of said QRS complex after said complex has passed through a bandpass filter having a center frequency of about 25 Hz; a SSA metric, which comprises a signed-square area metric in which a plurality of samples taken of said QRS complex are squared, their signs are restored, the signed squares are summed, the square root of the absolute value of the sum is taken, and the sign is restored thereto; a QRS metric, which comprises a QRS angle $\Theta$ calculated from the amplitude and temporal order of the largest positive and largest negative peaks of the QRS complex, as follows:

$r = abs$ (smaller peak) $\div$ (larger peak), $\Phi = arcos (r)$, and if the first peak is positive and larger, $\Theta = \Phi$,
if the first peak is positive and smaller, $\Theta = -\Phi$,
if the first peak is negative and larger, $\Theta = \Phi - 180$, and,
if the first peak is negative and smaller, $\Theta = 180 - \Phi$;
and, an ORD metric, which is defined as follows:
if the positive peak is first, ORD = smaller peak $\div$ larger peak, and
if the negative peak is first, ORD = $-$ smaller peak $\div$ larger peak.

3. A method according to claim 2, wherein said storing step includes a sub-step of storing a first set of at least three metrics that includes said MOD metric, said PKP metric and said NVE metric period.

4. A method according to claim 2, wherein, if one or more of the MOD, PVE, NVE, DIF, FIL and SSA metrics are selected from said group of metrics, said storing step includes a further sub-step of amplitude normalizing said one or more metrics by dividing the value thereof by the value of said PKP metric.

5. A method according to claim 1, including further steps, prior to said measuring and comparing steps, of:

filtering the patient's electrogram through a bandpass filter having a center frequency of about 25 Hz; and sampling said filtered electrogram at a predetermined rate to obtain said metrics.

6. A method according to claim 5, wherein:
said filtering of the patient's electrogram is performed through a filter having a pass band of 2 to 30 Hz.

7. A method according to claim 6, wherein said sampling step includes storing a peak value of said electrogram, and wherein said predetermined rate is about 80 Hz.

8. A method according to claim 6, wherein said storing step includes a sub-step of:

calculating and storing an NSR-mean value for each of the metrics of said first set, said NSR-mean value for each metric comprising the mean value of the metric during normal sinus rhythm of a normal electrogram.

9. A method according to claim 8, wherein said comparing step includes a sub-step of subtracting from each of the metrics in said second set of metrics the corresponding NSR-mean value therefor to provide NSR-mean-removed metrics corresponding to the patient's heart rhythm.

10. A method according to claim 9, wherein said comparing step includes a further sub-step of classifying a heartbeat as either normal or abnormal based on the value of one of said NSR-mean-removed metrics exceeding a predetermined threshold value.

11. A method according to claim 10, wherein said diagnosing step includes a sub-step of diagnosing the patient's heart rhythm as ventricular fibrillation if at least four heartbeats of ten successive heartbeats are classified as abnormal.

12. A method according to claim 1 wherein said diagnosing step includes a sub-step of diagnosing the patient's heart rhythm as sinus tachycardia if at least a specified number of a predetermined greater number of last heartbeats are classified as normal.

13. A method according to claim 1, wherein said diagnosing step includes a sub-step of diagnosing the patient's heart rhythm as sinus tachycardia if at least 8 of the last 10 heartbeats are classified as normal.

* * * * *